United States Patent [19]

Slaugh

[11] Patent Number: 5,030,784

[45] Date of Patent: Jul. 9, 1991

[54] PROCESS FOR CONVERTING LOWER-ALKYL SUBSTITUTED AROMATIC COMPOUNDS AND BUTADIENE TO 4-ARYL-1-BUTENE OR 4-ARYL-1-PENTENE AND PROPYLENE

[75] Inventor: Lynn H. Slaugh, Houston, Tex.

[73] Assignee: Shell Oil Company, Houston, Tex.

[21] Appl. No.: 484,300

[22] Filed: Feb. 26, 1990

[51] Int. Cl.$^5$ .......................... C07C 2/00; C07C 5/09; C07C 2/64; C07C 5/23

[52] U.S. Cl. .................................. 585/323; 585/435; 585/452; 585/439; 585/474; 585/664

[58] Field of Search ............... 585/323, 435, 452, 439, 585/474, 664

[56] References Cited

U.S. PATENT DOCUMENTS

| | | | |
|---|---|---|---|
| 3,244,758 | 4/1966 | Eberhardt | 585/452 |
| 3,953,535 | 4/1976 | Shima et al. | 585/452 |
| 4,018,840 | 4/1977 | Iwata et al. | 585/452 |
| 4,262,156 | 4/1981 | Banasiak | 585/645 |
| 4,331,559 | 5/1982 | Banasiak | 502/154 |

*Primary Examiner*—H. S. Sneed
*Assistant Examiner*—J. Saba

[57] ABSTRACT

The instant invention relates to a process for converting methyl- and/or ethyl-substituted benzene or naphthalene and butadiene to 4-aryl-1-butene or 4-aryl-1-pentene and propylene by:

a) reacting a methyl- and/or ethyl-substituted benzene or naphthalene and 1,3-butadiene in the presence of an alkali metal catalyst, b) reacting the butenylated reaction product of step a) with ethylene in the presence of of a disproportionation catalyst, and c) separating from the reaction product of step b) product 4-aryl-1-butene or 4-aryl-1-pentene and propylene.

8 Claims, No Drawings

PROCESS FOR CONVERTING LOWER-ALKYL SUBSTITUTED AROMATIC COMPOUNDS AND BUTADIENE TO 4-ARYL-1-BUTENE OR 4-ARYL-1-PENTENE AND PROPYLENE

FIELD OF THE INVENTION

This invention relates to a process for converting lower-alkyl substituted benzene or naphthalene plus butadiene to 4-aryl-1-butene or 4-aryl-1-pentene plus propylene.

BACKGROUND OF THE INVENTION

Butadiene is a commodity chemical, which, because of economic cycles, can be at times in surplus. When it is in surplus, it is desirable to convert it to higher value products. 4-Aryl-1-butenes and 4-aryl-1-pentenes, such as 4-phenyl-1-butene, 4-naphthyl1-butene, 4-phenyl-1-pentene and 4-naphthyl-1-pentene are valued specialty chemicals that, for example, can be used as components in specialty polymers, say by copolymerizing with stryene and/or divinylbenzene. These materials can also be used as feedstocks to prepare specialty detergents or lube stocks. Propylene, which is a coproduct of the instant process, has many uses, e.g.., in polymers such as polypropylene, as feedstocks to produce acids, alcohols, epoxides, etc.

SUMMARY OF THE INVENTION

The instant invention relates to a process for converting methyl-and/or ethyl-substituted benzene or naphthalene and butadiene to 4-aryl-1-butene or 4-aryl-1-pentene and propylene wherein said aryl moiety is phenyl or naphthyl and 1) contains one less methyl substituent than the starting benzene or naphthalene when the starting benzene or naphthalene contains at least one methyl substituent or 2) contains one less ethyl substituent than the starting benzene or naphthalene when the starting benzene or naphthalene contains only ethyl substituent(s), which process comprises:

a) reacting a methyl- and/or ethyl-substituted benzene or naphthalene and 1,3-butadiene in the presence of an alkali metal catalyst at a temperature ranging from about 0° C. to about 150° C., thereby producing a butenylated, b) reacting the butenylated reaction product of step a) with ethylene in the presence of a disproportionation catalyst at a temperature ranging from about −10° C. to about 100° C., thereby producing a disproportionated product and c) separating from the resulting product of step b) product 4-aryl-1-butene or 4-aryl-1-pentene and propylene.

DETAILED DESCRIPTION OF THE INVENTION

The starting benzenes and naphthalenes for the instant process are benzenes and naphthalenes that have been substituted with one or more methyl and/or ethyl substituents. Illustrative examples include the methyl-substituted benzenes such as, for example, toluene, the xylenes, 1,3,5-tri-methylbenzene, hexamethylbenzene, etc.; the ethyl-substituted benzenes such as, for example, ethylbenzene, the various diethylbenzenes, 1,2,5-triethylbenzene, hexaethylbenzene, etc.; the methyl/ethyl-substituted benzenes such as, for example, 1-methyl-3-ethylbenzene, 1,2-dimethyl-5-ethylbenzene, 1,2- dimethyl-4,5-diethylbenzene, the methyl-substituted naphthalenes such as, for example, 1-methylnaphthalene, 2-methylnaphthalene, 1,8-dimethylnaphthalene, 1,4-dimethylnaphthalene, 1,3,5-trimethylnaphthalene, hexamethylnaphthalene, etc.; the ethyl-substituted naphthalenes such as, for example, 1-ethylnaphthalene, 2-ethylnaphthalene, 1,2-diethylnaphthalene, 1,3-diethylnaphthalene, 1,4,5-triethylnaphthalene, 1,2,3,4,-tetraethylnaphthalene, etc.; and the methyl/ethyl-substituted naphthalenes such as, for example, 1-methyl-2-ethylnaphthalene, 1,2-di-methyl-5,6-diethylnaphthalene, 1,4-dimethy The starting benzenes and naphthalenes may, in addition to methyl and/or ethyl substituents, contain other substituents that are inert to the butenylation reaction, such as halo- and alkoxy-.

The first step of the instant process is to react the methyl-and/or ethyl-substituted benzenes or naphthalenes with 1,3-butadiene in the presence of a metallic alkali metal catalyst. While any of the Group IA metals can be utilized as a catalyst, sodium and potassium are preferred. The alkali metal catalyst can be utilized as such in a dispersed form in the reaction medium or, preferably, it is supported on a nonacidic oxide support. Group IA and Group IIA oxides are typically utilized as supports and preferably calcium oxide and sodium oxide are utilized. Alumina also provides a suitable support. Mixed metallic alkali metals can be utilized, such as a sodium-potassium mixture supported on calcium oxide.

The butenylation reaction is carried out at temperatures ranging from about 0° C. to about 150° C. and preferably from about 25° C. to about 130° C. Reaction pressures are not critical and will typically range from about atmospheric to about 100 bars.

The butenylation reaction may be carried out in a batch reactor or in a continuous flow reactor. For example, it may be carried out in a traditional fixed bed reactor, the bed comprising a supported metallic alkali metal catalyst, wherein reactant benzenes or naphthalenes and butadiene in a cocurrent or counter flow mode is passed over the bed to carry out the reaction. Trickle phase and continuous stirred tank reactors are also suitable. Other continuous reactor configurations will be readily apparent to one skilled in the art.

Batch reactors, such as autoclaves, are also suitable. For example, reactant benzenes or naphthalenes and catalyst are charged to an autoclave which is then pressured with butadiene and heated to the reaction temperature to allow the reaction to be carried out. Alternatively, reactant benzenes or naphthalenes and catalyst are charged to a stirred tank reactor and butadiene is bubbled through the reaction at reaction temperature in order to carry out the reaction.

To avoid multiple butenylated products the molar ratio of reactant benzene or naphthalene to butadiene is kept at greater than one. Batch reactions utilizing an excess of the alkylaromatic reactant in conjunction with a controlled addition of the butadiene yield a monobutenylated product exclusively.

After reaction is complete, the reaction mixture can be treated to remove any remaining catalyst by well known means, such as filtration, with or without decomposition of the catalyst, flash distillation, etc. At this point, butenylated reaction product can be separated from the reaction mixture by traditional means such as distillation or fractional crystallization and the butenylated benzene or naphthalene passed on to the second, or ethenolysis step of the instant process. Alternatively, the reaction mixture can be flashed to remove unreacted butadiene, and the resulting product passed on to the ethenolysis step.

The major product of the butenylation reaction will be 5-aryl-2pentene or 5-aryl-2-hexene, depending on whether butenylation occurs at a methyl moiety or an ethyl moiety.

The second step of the instant process comprises reacting the butenylated reaction product of the first step with ethylene in the presence of a disproportionation catalyst. The disproportionation catalysts employed in the second step of the instant process are also known in the prior art. Any solid catalyst system which is capable of promoting or catalyzing the olefin disproportionation reaction of butene-2 and ethylene to propylene is suitable. Preferably the disproportionation catalyst is one of molybdenum, tungsten and/or rhenium oxide supported on a refractory oxide support, preferably alumina. U.S. Pat. No. 3,261,879 discloses a molybdenum oxide-promoted catalyst. U.S. Pat. No. 3,365,513 discloses a tungsten oxide-promoted catalyst. A rhenium oxide-promoted catalyst is disclosed in British Patent 1,054,864. A rhenium oxide, molybdenum and/or tungsten oxide-promoted catalyst is disclosed in British patent 1,338,429. As reported in the prior art, these solid catalysts can also contain minor amounts of various treating agents, such trialkylaluminum compounds, dialkylaluminum halides, mono- and polyvalent alcohols, and the like. It is also sometimes advantageous to treat the solid catalyst with suitable gases, such as carbon dioxide, hydrogen and the like. The disproportionation catalysts can also be treated with the alkaline earth and alkali metal compounds as reported in the prior art. Preferably, a compound of sodium or potassium is used. Rhenium catalysts have also been promoted with tin compounds, such as tin oxide. Tetraalkyl tin compounds have also been utilized as promoters. The tetraalkyl tin compounds (alkyl being lower alkyl of $C_1$–$C_8$) are added to the reaction mixture to increase the activity of the rhenium catalyst. Tetramethyl tin, tetraethyl tin, tetrapropyl tin and tetrabutyl tin compounds are frequently utilized. An alumina supported rhenium catalyst promoted by tetraalkyl tin, preferably tetrabutyl tin, is a preferred catalyst for the ethenolysis reaction.

The ethenolysis reaction is carried out at temperatures ranging from about $-10°$ C. to about $100°$ C., preferably from about $0°$ C. to about $80°$ C., more preferably from about $20°$ C. to about $50°$ C. Reaction pressures are not critical and will typically range from about atmospheric to about 100 bars.

The ethenolysis reaction may be carried out in a batch reactor or in a continuous flow reactor. For example, it may be carried out in a traditional fixed bed reactor, the bed comprising the supported disproportionation catalyst, wherein the alkenylated product from the alkenylation reaction is passed over the bed to carry out the reaction. Trickle phase and continuous stirred tank reactors are also suitable. Other continuous reactor configurations will be readily apparent to one skilled in the art.

Batch reactors, such as autoclaves, are also suitable. For example, alkenylated product from the alkenylation reaction and catalyst are charged to an autoclave which is then pressured with ethylene and heated to the reaction temperature to allow the reaction to be carried out. Alternatively, alkenylated product from the alkenylation reaction and catalyst are charged to a stirred tank reactor and ethylene is bubbled through the reaction at reaction temperature in order to carry out the reaction.

After reaction is complete, the reaction mixture can be treated to remove any remaining catalyst by well known means, such as filtration or centrifugation. At this point, the 4-aryl-1-butenes and 4-aryl-1-pentenes and propylene can be separated from the reaction mixture by traditional means. For example, flash distillation can be used to remove the propylene and unreacted ethylene and fractional distillation can be used separate out the aryl-substituted butenes and pentenes.

Inert solvents such as alkanes, e.g., cyclohexane, dodecane, hexadecane, etc., can be utilized in either or both of the butenylation or ethenolysis steps.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described by the following examples which are provided for illustrative purposes and are not to be construed as limiting the invention.

ILLUSTRATIVE EMBODIMENT I

A. Alkenylation Reaction

Catalyst Preparation:

Finely powdered calcium oxide was heated in a quartz tube to $575°$ C. under a flow of dry nitrogen (200 ml/min). The freshly calcined calcium oxide (50 g) was placed in a 500 ml single neck Morton flask with 1.5 g of sodium metal chips under a nitrogen atmosphere. The mixture was heated to about $200°$–$240°$ C. and tumbled on a rotary evaporator for 3 hours under an argon atmosphere to give a uniform grey-purple powder.

Reaction:

The freshly prepared sodium on calcium oxide catalyst (5Og) was placed under a nitrogen atmosphere in a 500 ml three necked flask equipped with an air stirrer, reflux condenser, thermometer, gas inlet tube for the introduction of nitrogen and 1,3-butadiene and a gas outlet tube. Dry toluene (185g, 2.0 mole) was added to the catalyst and the mixture was stirred and heated to 90-95° C under a nitrogen blanket. Butadiene (49g, 0.91 mole) was bubbled through the stirred mixture over a period of 7 hours at $90°$–$95°$ C.

The reaction mixture was cooled to $20°$ C. and the catalyst was destroyed by the slow addition of isopropyl alcohol. The reaction mixture was filtered through a celite pad and the solids were washed with toluene. The toluene wash and filtrates were combined and washed with deionized water until neutral and then dried over magnesium sulfate. Filtration followed by distillation via a 6" vigrux column yielded 28.3 g (10% yield based on conversion of toluene and 22% yield based on conversion of butadiene) of a colorless oil ( b.p. $199°$–$210°$ C.). Analysis by gas chromatography, GC/MS and $^{13}C$ NMR showed the product to be 94% 5-phenyl-2-pentene (mixture of cis and trans isomers), 4% 5-phenyl-1-pentene and less than 1% 1-phenyl-1-pentene.

B. Ethenolysis Reaction:

Catalyst:

The catalyst was a 15%RE$_2$O$_7$/alumina material which had been activated by heating at 540° C. for 2.5 hours under an air flow of 20 l/hr followed by heating at 540° C under a nitrogen flow of 20 l/hr for 1.5 hours.

Reaction.

To a nitrogen-purged 100 ml hoke addition vessel was added a nitrogen purged solution of about 12.5g (0.1 mole) of 90% 5-phenyl-2-pentene and 12.5g of dry, nitrogen-purged hexadecane and 1.6ml (5 mmole) of tetrabutyl tin under a nitrogen atmosphere. To a 100 ml Parr autoclave, under a nitrogen atmosphere, was added 6.0g (5 mmole of rhenium) of the activated rhenium oxide/alumina catalyst. The hoke addition vessel was affixed to the Parr autoclave and the contents of the hoke vessel were pressured into the autoclave with 500 psi of ethylene at room temperature. The reaction mixture was stirred for 16 hours under 500 psi ethylene pressure, cooled to 5° C. and then the gas pressure was vented off through a gas sample vessel. Analysis of the liquid fraction of the reaction mixture by GS/MS, gas chromatography and $^{13}$C NMR established a 95% conversion of the 5-phenyl-2-pentene to 4-phenyl-1-butene. Analysis of the gas sample by GC/MS showed it to consist primarily of propylene.

ILLUSTRATIVE EMBODIMENT II

The use of ethylbenzene as a feedstock instead of toluene in a process similar to Illustrative Embodiment I will result in a product containing substantial amounts of 4-phenyl-1-pentene.

ILLUSTRATIVE EMBODIMENT III

The use of 1-methylnaphthalene as a feedstock instead of toluene in a process similar to Illustrative Embodiment I will result in a product containing substantial amounts of 4-naphthyl-1-butene.

ILLUSTRATIVE EMBODIMENT IV

The use of 1-ethylnaphthalene as a feedstock instead of toluene in a process similar to Illustrative Embodiment I will result in a product containing substantial amounts of 4-naphthyl-1-pentene.

What is claimed is:

1. A process for converting methyl-and/or ethyl-substituted benzene or naphthalene and butadiene to 4-aryl-1-butene or 4-aryl-1-pentene and propylene wherein said aryl moiety is phenyl or naphthyl and 1) contains one less methyl substituent than the starting benzene or naphthalene when the starting benzene or naphthalene contains at least one methyl substituent or 2) contains one less ethyl substituent than the starting benzene or naphthalene when the starting benzene or naphthalene contains only ethyl substituent(s), which process comprises:
   a) reacting the methyl-and/or ethyl-substituted benzene or naphthalene and 1,3-butadiene in the presence of an alkali metal catalyst,
   b) reacting the butenylated reaction product of step a) with ethylene in the presence of a disproportionation catalyst comprising rhenium oxide supported on alumina wherein the disproportionation catalyst is promoted with tetraalkyltin, and
   c) separating from the resulting product of step b) product 4-aryl-1-butene or 4-aryl-1-pentene and propylene."

2. The process of claim 1 wherein step a) is carried out at a temperature ranging from about 0° C. to about 150° C. and step b) is carried out at a temperature ranging from about −10° C. to about 100° C.

3. The process of claim 2 wherein step a) is carried out at a temperature ranging from about 25° C. to about 130° C. and step b) is carried out at a temperature ranging from about 0° C. to about 80° C.

4. The process of any one of claims 1–3 wherein the alkali metal catalyst comprises sodium or potassium deposited on calcium oxide or aluminum oxide.

5. The process of claim 1 wherein the tetraalkyl tin is selected from tetramethyl tin, tetraethyl tin, tetrapropyl tin, tetrabutyl tin and mixtures thereof.

6. The process of claim 5 wherein the tetraalkyl tin is tetrabutyl tin.

7. The process of any one of claims 1–3 wherein toluene is reacted with butadiene.

8. The process of any one of claims 1–3 wherein the molar ratio of benzene or naphthalene to butadiene is greater than 1.

* * * * *